United States Patent
Johnson

(10) Patent No.: US 12,259,350 B2
(45) Date of Patent: Mar. 25, 2025

(54) SENSOR ASSEMBLY AND METHOD OF SENSING WATER IN A FLUID

(71) Applicant: DEERE & COMPANY, Moline, IL (US)

(72) Inventor: Kevin J. Johnson, Waverly, IA (US)

(73) Assignee: DEERE & COMPANY, Moline, IL (US)

( * ) Notice: Subject to any disclaimer, the term of this patent is extended or adjusted under 35 U.S.C. 154(b) by 214 days.

(21) Appl. No.: 18/052,953

(22) Filed: Nov. 7, 2022

(65) Prior Publication Data

US 2024/0151676 A1     May 9, 2024

(51) Int. Cl.
| | |
|---|---|
| G01N 27/22 | (2006.01) |
| G01N 27/07 | (2006.01) |
| G01N 33/28 | (2006.01) |
| G01R 27/08 | (2006.01) |
| G01R 27/26 | (2006.01) |

(52) U.S. Cl.
CPC ....... *G01N 27/226* (2013.01); *G01N 33/2835* (2013.01)

(58) Field of Classification Search
CPC ........ G01N 27/07; G01N 27/22; G01N 33/18; G01N 33/28; G01R 27/08; G01R 27/26
See application file for complete search history.

(56) References Cited

U.S. PATENT DOCUMENTS

| | | | |
|---|---|---|---|
| 4,517,547 A | | 5/1985 | Gray et al. |
| 5,513,527 A | * | 5/1996 | Griffiths .................. G01F 23/26 701/1 |
| 5,564,904 A | * | 10/1996 | Heckman ................ G01M 3/16 73/61.43 |
| 10,234,441 B2 | * | 3/2019 | Sanet ..................... G01N 27/07 |
| 2011/0259802 A1 | * | 10/2011 | Wieczorek ......... G01N 33/2847 73/304 R |
| 2013/0031963 A1 | * | 2/2013 | Ritchie, Jr. ........ G01N 33/2847 73/61.43 |
| 2014/0077825 A1 | | 3/2014 | Coleman et al. |
| 2022/0094118 A1 | | 3/2022 | Ritchie, Jr. |

* cited by examiner

*Primary Examiner* — Neel D Shah

(57) ABSTRACT

A sensor assembly and method of sensing water in a fluid may include a sensor body having a first electrical connection, a second electrical connection, and a probe portion configured to be submerged in a fluid comprising a fuel, a signal input line supplying a signal voltage and power to the sensor from a voltage source to the first electrical connection of the sensor body, a ground line connected to the second electrical connection of the sensor body, and a controller configured to receive a signal output from the signal input line for determining a presence of water in the fluid.

16 Claims, 2 Drawing Sheets

SENSOR ASSEMBLY AND METHOD OF SENSING WATER IN A FLUID

BACKGROUND

Water-in-fuel (WIF) sensors may be used to detect or sense the presence of water in a fuel or other fluid, such as a nonsoluble fluid with a low dielectric constant. WIF sensors may be passive sensors that rely on dissolved solids in the water to create an electrically conductive path through the water in order to determine that water is present. WIF sensors may indicate through an electronic control unit (ECU) or other controller to an operator of a vehicle fueled by the fluid or otherwise generate and/or transmit an output signal if water is sensed in the fluid. In at least one example, water is separated from the fluid and accumulates in a collection bowl to a level that is detected by the sensor.

SUMMARY

According to an aspect of the present disclosure, a sensor assembly includes a sensor body having a first electrical connection, a second electrical connection, and a probe portion configured to be submerged in a fluid comprising a fuel, a signal input line supplying a signal voltage and power to the sensor from a voltage source to the first electrical connection of the sensor body, a ground line connected to the second electrical connection of the sensor body, and a controller configured to receive a signal output from the signal input line for determining a presence of water in the fluid.

The controller may be configured to output a controller signal indicating a threshold level of water in the fluid. The sensor body may include a housing configured to electrically insulate a probe inside the probe portion from the fluid. The sensor body may be configured such that the fluid surrounds the probe portion of the sensor body. The signal voltage may be between 2 volts (V) and 6 V. The assembly may further include a sensor resistance between the first electrical connection of the sensor body and the second electrical connection of the sensor body. The assembly may further include a signal line resistor between the voltage source and the signal input line. The assembly may further include a signal output line connecting the signal input line to the controller and configured to output the signal output to the controller. The sensor body may include two electrical connections consisting of the first electrical connection and the second electrical connection. The sensor body may include a capacitive sensor generating an electromagnetic field.

According to an aspect of the present disclosure, a method of sensing water in a fluid includes providing a sensor body having a first electrical connection, a second electrical connection, and a probe generating an electromagnetic field, submerging the probe in the fluid comprising a fuel, supplying a voltage through a signal input line that connects a voltage source to the first electrical connection, receiving a signal output at a signal output line connected to the signal input line, and determining the presence of water in the fluid based on the signal output.

Determining the presence of water in the fluid based on the signal output may include determining the presence of water in the fluid based on an operating current of the signal output. Determining the presence of water in the fluid based on the signal output may include determining the presence of water in the fluid based on an output voltage of the signal output. The voltage may be between 2V and 6V. The method may further include electrically insulating the probe from the fluid. The method may further include decreasing an output voltage of the signal output when water is present in the fluid relative to the output voltage of the signal output when water is not present in the fluid. The method may further include increasing an operating current of the signal output when water is present in the fluid relative to the operating current of the signal output when water is not present in the fluid.

Other features and aspects will become apparent by consideration of the detailed description, claims, and accompanying drawings.

BRIEF DESCRIPTION OF THE DRAWINGS

The detailed description of the drawings refers to the accompanying figures.

Like reference numerals are used to indicate like elements throughout the several figures.

DETAILED DESCRIPTION

Figure 1:
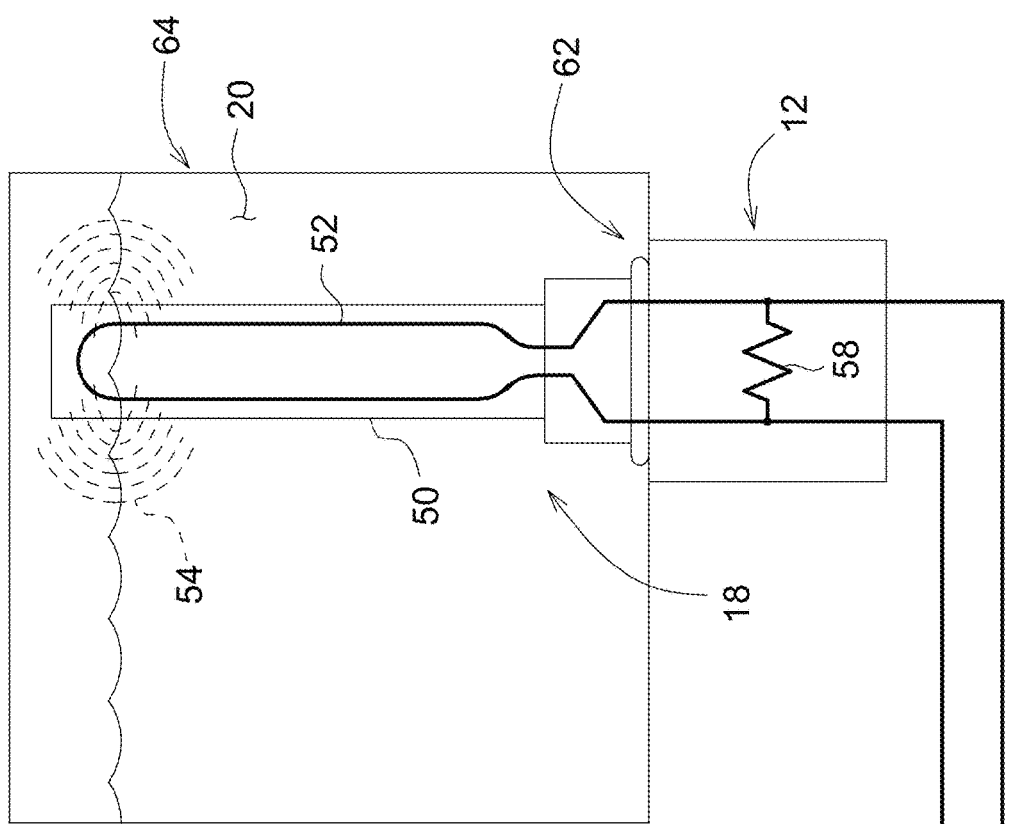
FIG. 1 illustrates a sensor assembly in accordance with an embodiment of the present disclosure.
Figure 1:
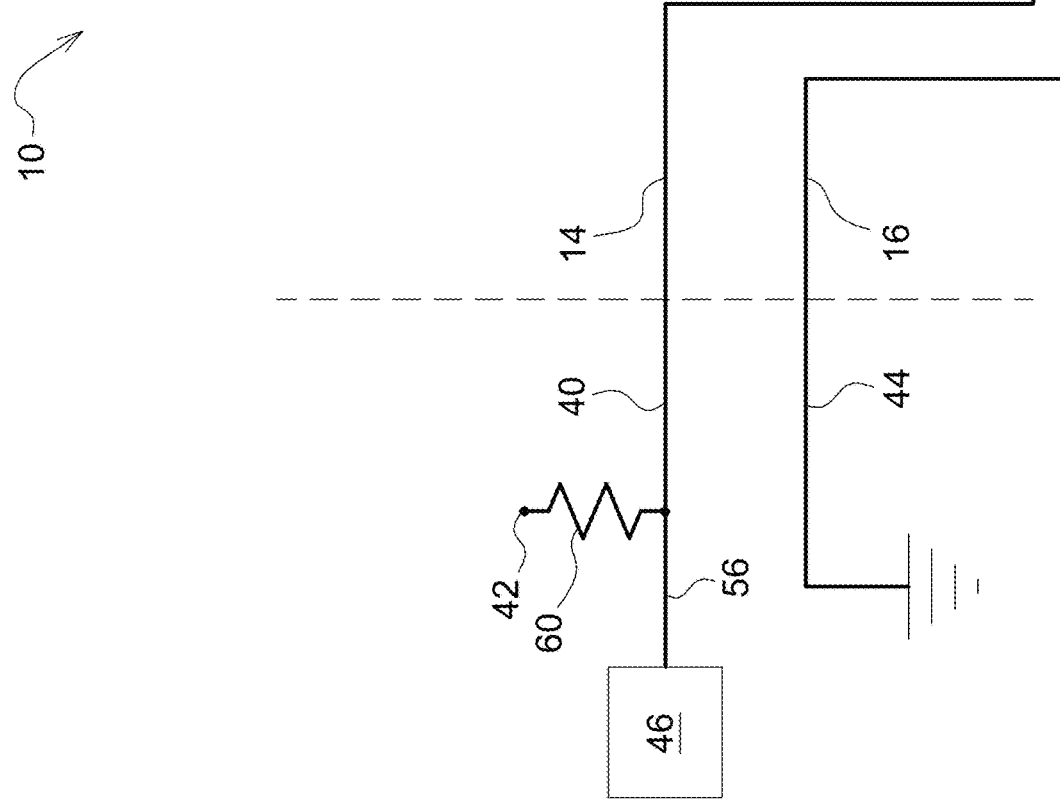

Referring to FIG. 1, a sensor assembly 10 is illustrated in accordance with an embodiment of the present disclosure. The assembly 10 of the illustrated embodiment is a water-in-fuel sensor assembly that includes a sensor body 12. The sensor body 12 includes a probe portion 18. The probe portion 18 is submerged or configured to be submerged in a fluid 20. As illustrated in FIG. 1, the probe portion 18 is inserted from a lower end 62 of a water collection bowl 64. The water of the illustrated embodiment separates from the fluid 20 and collects at the lower end 62 of the water collection bowl 64. The fluid 20 is a fuel in the illustrated embodiment, such as gasoline, diesel fuel, kerosene, and/or one or more liquid or gas fuels as non-limiting examples. The fluid 20 in the illustrated embodiment may include water. Presence of water in the fluid 20 is detected or determined in accordance with embodiments of the present disclosure.

The sensor body 12 includes a first electrical connection 14 and a second electrical connection 16. In the illustrated embodiment, the first electrical connection 14 and the second electrical connection 16 are the only two electrical connections of the sensor body 12 and/or the sensor assembly 10. Accordingly, the assembly 10 and/or the sensor body 12 may be used as a direct replacement for or interchangeably with passive or unpowered two-wire sensors. In one or more additional embodiments not illustrated, the assembly 10 and/or the sensor body 12 utilizes more than two electrical connections and/or wires. In the illustrated embodiment, the two electrical connections 14, 16 are the signal input or voltage input and ground connection.

The assembly 10 further includes a signal input line 40 supplying a signal voltage from a voltage source 42 to the first electrical connection 14 of the sensor body 12. In the illustrated embodiment, the voltage source 42 is 5 volts or a voltage between 4 and 6 volts. The signal voltage is between 2 volts and 6 volts in the illustrated embodiment. The signal voltage is between 0 and 12 volts in another embodiment. The signal voltage is greater than 12 volts in a further embodiment. In an embodiment, the output voltage is between 3 volts and 4 volts when water is detected and between 4.1 volts and 4.8 volts when water is not detected.

In a further embodiment, any voltage step change, from a lower voltage when water is detected to a higher voltage when water is not detected, indicates that water is detected.

The assembly 10 further includes a ground line 44 connected to the second electrical connection 16 of the sensor body 12. The ground line 44 acts as a power return and signal reference in an embodiment of the assembly 10.

The assembly 10 further includes a controller 46. The controller 46 receives a signal output from the signal input line 40 for determining the presence of water in the fluid 20 or otherwise monitors the signal input line 40 at a signal pin of the assembly 10 for a voltage change that would indicate that water is present. In the illustrated embodiment, the signal output is sent to the controller 46 via a signal output line 56 that is connected to the signal input line 40 and outputs the signal output to the controller 46. The signal output in the illustrated embodiment is an indication, measurement, or determination of voltage at the signal input line 40. In additional embodiments, the signal output is an indication, measurement, or determination of current at the signal input line 40. The controller 46 of the illustrated embodiment, and/or another portion of the assembly 10, Includes an analog/digital converter to convert the analog value at the signal input line 40 to a digital value for processing or other action by the controller 46. In embodiments not illustrated, one or more of the voltage source 42, the signal input line 40, the ground line 44, and/or one or more other components or portions identified herein form(s) part of the controller 46.

The assembly 10 further includes a sensor resistance, illustrated as a sensor resistor 58 in FIG. 1, between the first electrical connection 14 of the sensor body 12 and the second electrical connection 16 of the sensor body 12. The sensor resistor 58 represents resistance or electrical load by sensor electronics used to detect the water and to change the signal output by lowering the resistance value, as described further herein. By way of non-limiting example, in the illustrated embodiment, when water is not detected, the sensor resistor 58 or sensor electronics provide 220 Kohms of resistance or between 200 and 250 Kohms at a voltage of 4.78 volts or between 4 and 6 volts. When water is detected in the illustrated embodiment, the sensor resistor 58 or sensor electronics provide 38 Kohms of resistance or between 30 and 50 Kohms at a voltage of 3.95 volts or between 3 and 5 volts.

The assembly 10 further includes a signal line resistor 60 between the voltage source 42 and the signal input line 40. The signal line resistor 60 acts with the voltage source 42 and the sensor to form a voltage divider to generate the signal output, such as a reference voltage, to the controller 46. In an embodiment, when water is not detected by the sensor body 12, the signal line resistor 60 carries the load of the assembly 10. Power is sent through the signal line resistor 60 to the sensor body 12, and the signal line resistor 60 is a means to indicate the status of the sensor body 12. Signal line resistor 60 may act as a current to voltage converter in an embodiment. The signal line resistor 60 creates an electrical load when voltage is applied from the voltage source 42. This electrical load current results in a voltage drop across the signal line resistor 60, which is detected, measured, or otherwise determined by the controller 46 as the signal output as a voltage. When water is detected, the sensor body 12 increases its load, which results in a detectable voltage change as the signal output. The value of the signal line resistor 60 in the illustrated embodiment depends on the power needed by the sensor body 12 to operate. In the illustrated embodiment, the signal line resistor 60 operates as a current-to-voltage converter for reading or otherwise receiving by the controller 46.

The controller 46 of an embodiment further outputs a controller signal 48 indicating the presence of water in the fluid 20. The controller signal 48 may include a signal to provide a message, alert, or similar indication to an operator of a vehicle (not shown) powered by fuel of/in the fluid 20, a signal that service may be required or for derating, modifying, or otherwise controlling or changing a control of the vehicle, a fuel system, or an engine or other power system in non-limiting examples.

The sensor body 12 includes a probe 52 positioned inside or otherwise forming part of the probe portion 18. The sensor body 12 of the illustrated embodiment includes a capactive sensor. The capacitive sensor of an embodiment is an electromagnetic field 54 from the probe 52 from transfer of charge between two isolated metallic plates (not shown). The rate of charge is proportional to the dielectric level of the fluid 20. High dielectric water collects at the lower end 62 of the water collection bowl 64 and displaces low dielectric fuel or other non-water fluid. If the water level reaches the end of the probe portion 18, the sensor body 12 detects the changed dielectric level and indicates the signal output to the controller 46. In accordance with some embodiments, a threshold level of the water is or includes the level or point where the sensor body 12 detects the changed dielectric level and/or the water level reaches the end of the probe portion 18.

The sensor body 12 increases its draw of operating current when water is present in the fluid 20 relative to the operating current when water is not present in the fluid 20. When the operating current increases, the sensor body 12 operates at a lower supply voltage. Therefore, the operating current of the signal output is increased when water is present in the fluid 20, but an output voltage of the signal output is decreased when water is present. In an embodiment, current flows only from the voltage source 42 to the first electrical connection 14, and from the first electrical connection 14 to the second electrical connection 16 or to ground. In other words, in an embodiment, no current flows out of the sensor body 12 except to ground.

The sensor body 12 includes a housing 50 electrically insulating the probe 52 and/or one or more electrically conductive portions inside the probe portion 18 from the fluid 20. The fluid 20 surrounds the probe portion 18 of the sensor body 12 in the illustrated embodiment.

Figure 2:
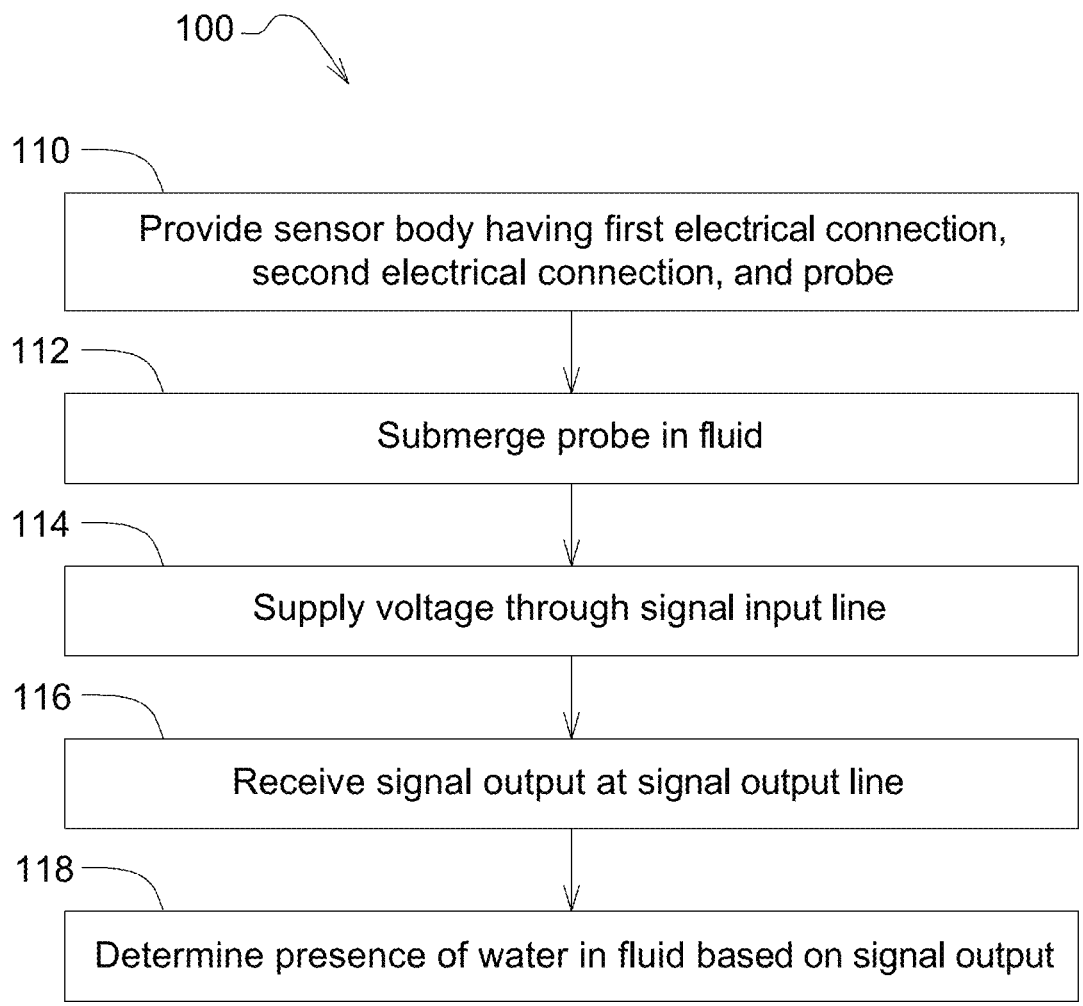
FIG. 2 illustrates a method of sensing water in a fluid in accordance with an embodiment of the present disclosure.

Referring now to FIG. 2, a method 100 of sensing water in the fluid 20 is illustrated in accordance with an embodiment of the present disclosure. The method 100 includes providing, at step 110, the sensor body 12 having the first electrical connection 14, the second electrical connection 16, and the probe 52. The probe 52 in the illustrated embodiment includes or is part of a capacitive sensor but may include a different sensor component or operate according to a different principle in additional embodiments. The method 100 further includes submerging, at step 112, the probe 52 in the fluid 20. The fluid 20 includes fuel in the illustrated embodiment and may include one or more other or additional fluids. The method 100 further includes supplying, at step 114, a voltage through the signal input line 40 that connects the voltage source 42 to the first electrical connection 14. The method 100 further includes receiving, at step 116, the signal output at the signal output line 56 connected to the signal input line 40. The method 100 further includes determining, at step 118, the presence of water in the fluid 20 based on the signal output.

In an embodiment, determining the presence of water in the fluid 20 based on the signal output includes determining the presence of water in the fluid 20 based on an operating current of the signal output. In another embodiment, determining the presence of water in the fluid 20 based on the signal output includes determining the presence of water in the fluid 20 based on an output voltage of the signal output.

The method 100 of an embodiment includes electrically insulating the probe 52 from the fluid 20, such as further described in embodiments herein.

The method 100 of an embodiment includes decreasing an output voltage of the signal output when water is present in the fluid 20 relative to the output voltage of the signal output when water is not present in the fluid 20. Similarly, the method 100 of an embodiment includes increasing an operating current of the signal output when water is present in the fluid 20 relative to the operating current of the signal output when water is not present in the fluid 20.

The method 100 of embodiments described herein includes any one or more features or structures of one or more embodiments of the assembly 10, and the assembly 10 of embodiments described herein includes any one or more steps or details of one or more embodiments of the method 100.

Without in any way limiting the scope, interpretation, or application of the claims appearing below, a technical effect of one or more of the embodiments disclosed herein is sensing or determining the presence of water in a fuel with the sensor assembly 10 that may directly replace and/or be interchangeable with a conventional two-wire passive sensor or an active sensor that is traditionally a 3-wire device. The assembly 10 of embodiments utilizes the voltage source 42, having a relatively low voltage and/or current for signal input to a conventional passive sensor, to both supply power to the sensor body 12 for generation of the electrical field and generate a signal input that is detected or measured at the signal input line 40 to determine the presence of water in the fluid 20. Therefore, a third line or wire powering the sensor body 12 is not necessary. Further, the capacitive principle of operation of the assembly 10 allows the probe 52 and other sensing or electrically conductive portions of the assembly 10 to avoid or eliminate contact with the water, fuel, or other contents of the fluid 20. As such, the sensing, electrically conductive, or other portions that may be prone to corrosion, chemical reaction, or wear are not exposed to the water, fuel, or other contents of the fluid 20 that may cause such corrosion, chemical reaction, or wear. Therefore, the assembly 10 has improved reliability and durability.

The accuracy of the assembly 10 and the method 100 described in the embodiment herein is improved over conventional sensors. Conventional sensors cannot detect water directly because water may need a certain amount of dissolved solids and other impurities in the water to create an electrically conductive path to determine if water is present. Because the sensor described in embodiments herein is a capacitive sensor, does not rely on dissolved solids or contaminants in the water, and can detect water directly in the fluid 20, the assembly 10 and method 100 of the present embodiments provide a more accurate solution for sensing or detecting water in the fluid 20.

As used herein, "e.g." is utilized to non-exhaustively list examples and carries the same meaning as alternative illustrative phrases such as "including," "including, but not limited to," and "including without limitation." Unless otherwise limited or modified, lists with elements that are separated by conjunctive terms (e.g., "and") and that are also preceded by the phrase "one or more of" or "at least one of" indicate configurations or arrangements that potentially include individual elements of the list, or any combination thereof. For example, "at least one of A, B, and C" or "one or more of A, B, and C" indicates the possibilities of only A, only B, only C, or any combination of two or more of A, B, and C (e.g., A and B; B and C; A and C; or A, B, and C).

Those having ordinary skill in the art will recognize that terms such as "above," "below," "upward," "downward," "top," "bottom," etc., are used descriptively for the figures, and do not represent limitations on the scope of the disclosure, as defined by the appended claims. Furthermore, the teachings may be described herein in terms of functional and/or logical block components and/or various processing steps. It should be realized that such block components may be comprised of any number of hardware, software, and/or firmware components configured to perform the specified functions.

Terms of degree, such as "generally", "substantially" or "approximately" are understood by those of ordinary skill to refer to reasonable ranges outside of a given value or orientation, for example, general tolerances or positional relationships associated with manufacturing, assembly, and use of the described embodiments. The steps of determining, measuring, or sensing, as described in any methods or functions of embodiments described herein, may be used interchangeably in one or more embodiments of the present disclosure.

While the above describes example embodiments of the present disclosure, these descriptions should not be viewed in a limiting sense. Rather, other variations and modifications may be made without departing from the scope and spirit of the present disclosure as defined in the appended claims.

What is claimed is:

1. A sensor assembly, comprising:
   a sensor body having a first electrical connection, a second electrical connection, and a probe portion configured to be submerged in a fluid comprising a fuel;
   wherein the sensor body comprises only two electrical connections consisting of the first electrical connection and the second electrical connection;
   a signal input line supplying a signal voltage and power to the sensor from a voltage source to the first electrical connection of the sensor body;
   a ground line connected to the second electrical connection of the sensor body; and
   a controller configured to receive a signal output from the signal input line for determining a presence of water in the fluid.

2. The assembly of claim 1, wherein the controller is further configured to output a controller signal indicating a threshold level of water in the fluid.

3. The assembly of claim 1, wherein the sensor body comprises a housing configured to electrically insulate a probe inside the probe portion from the fluid.

4. The assembly of claim 3, wherein the sensor body is configured such that the fluid surrounds the probe portion of the sensor body.

5. The assembly of claim 1, wherein the signal voltage is between 2 V and 6 V.

6. The assembly of claim 1, further comprising a sensor resistance between the first electrical connection of the sensor body and the second electrical connection of the sensor body.

7. The assembly of claim 1, further comprising a signal line resistor between the voltage source and the signal input line.

8. The assembly of claim 1, further comprising a signal output line connecting the signal input line to the controller and configured to output the signal output to the controller.

9. The assembly of claim 1, wherein the sensor body comprises a capacitive sensor generating an electromagnetic field.

10. A method of sensing water in a fluid, the method comprising:
 providing a sensor body having a first electrical connection, a second electrical connection, and a probe generating an electromagnetic field, wherein the sensor body comprises only two electrical connections consisting of the first electrical connection and the second electrical connection;
 connecting the second electrical connection to a ground line;
 submerging the probe in the fluid comprising a fuel;
 supplying a voltage through a signal input line that connects a voltage source to the first electrical connection;
 receiving a signal output at a signal output line connected to the signal input line; and
 determining the presence of water in the fluid based on the signal output received from the signal output line via the signal input line connecting the voltage source and the first electrical connector.

11. The method of claim 10, wherein determining the presence of water in the fluid based on the signal output comprises determining the presence of water in the fluid based on an operating current of the signal output.

12. The method of claim 10, wherein determining the presence of water in the fluid based on the signal output comprises determining the presence of water in the fluid based on an output voltage of the signal output.

13. The method of claim 10, wherein the voltage is between 2V and 6V.

14. The method of claim 10, further comprising electrically insulating the probe from the fluid.

15. The method of claim 10, further comprising decreasing an output voltage of the signal output when water is present in the fluid relative to the output voltage of the signal output when water is not present in the fluid.

16. The method of claim 10, further comprising increasing an operating current of the signal output when water is present in the fluid relative to the operating current of the signal output when water is not present in the fluid.

* * * * *